United States Patent [19]
Whitbourne et al.

[11] Patent Number: 5,525,348
[45] Date of Patent: *Jun. 11, 1996

[54] COATING COMPOSITIONS COMPRISING PHARMACEUTICAL AGENTS

[75] Inventors: Richard J. Whitbourne, Fairport; Margaret A. Mangan, Rochester, both of N.Y.

[73] Assignee: STS Biopolymers, Inc., Henrietta, N.Y.

[ * ] Notice: The term of this patent shall not extend beyond the expiration date of Pat. No. 5,069,899.

[21] Appl. No.: 333,616

[22] Filed: Nov. 2, 1994

Related U.S. Application Data

[63] Continuation of Ser. No. 662,452, Feb. 28, 1991, abandoned, which is a continuation-in-part of Ser. No. 551,924, Jul. 12, 1990, abandoned, which is a continuation-in-part of Ser. No. 430,340, Nov. 2, 1989, Pat. No. 5,069,899.

[51] Int. Cl.$^6$ ........................................................ A61F 2/02
[52] U.S. Cl. .......................... 424/423; 514/781; 523/112; 523/113
[58] Field of Search .................. 424/423, 94.64, 424/78.24, 78.27; 514/834, 781; 536/21; 523/112, 113; 623/1, 3, 900; 604/187, 313, 319

[56] References Cited

U.S. PATENT DOCUMENTS

| | | | |
|---|---|---|---|
| 3,695,921 | 10/1972 | Shepherd et al. | 427/2 |
| 3,844,989 | 10/1974 | Harumiya et al. | 523/112 |
| 4,100,309 | 7/1978 | Micklus et al. | 427/2.28 |
| 4,119,094 | 10/1978 | Micklus et al. | 128/844 |
| 4,127,647 | 11/1978 | Sato et al. | 424/115 |
| 4,442,133 | 4/1984 | Greco et al. | 427/2 |
| 4,676,975 | 6/1987 | McGary et al. | 424/423 |
| 4,678,660 | 7/1987 | McGary et al. | 424/423 |
| 4,769,013 | 7/1988 | Lorenz et al. | 604/265 |
| 4,847,324 | 7/1989 | Creasy | 525/57 |
| 5,001,009 | 3/1991 | Whitbourne | 428/412 |
| 5,013,717 | 5/1991 | Solomon et al. | 514/56 |
| 5,061,738 | 10/1991 | Solomon et al. | 514/56 |
| 5,069,899 | 12/1991 | Whitbourne et al. | 424/94.64 |
| 5,331,027 | 7/1994 | Whitbourne | 524/37 |

FOREIGN PATENT DOCUMENTS

| | | |
|---|---|---|
| 0184465 | 6/1986 | European Pat. Off. . |
| 0231573 | 8/1987 | European Pat. Off. . |
| 0328421 | 8/1989 | European Pat. Off. . |
| 0338418 | 10/1989 | European Pat. Off. . |
| 8600795 | 2/1986 | WIPO . |
| 8905138 | 6/1989 | WIPO . |
| 9003768 | 4/1990 | WIPO . |

OTHER PUBLICATIONS

Lorenz et al., "The Use of Hydromer Coatings on Medical Devices", presented at The Medical Plastics Technology Seminar, Oct. 4, 1984, Ann Arbor, Mich., pp. 1–7.
Kurt Amplatz, MD; A Simple Non–thrombogenic Coating.

*Primary Examiner*—Carolos Azpuru
*Attorney, Agent, or Firm*—Michael A. Gollin

[57] ABSTRACT

Anti-thrombogenic, and/or anti-microbial and/or pharmaceutical compositions containing heparin and/or antibiotics and/or other pharmaceutical agents which may be reacted with quaternary ammonium components or other ionic surfactants and bound with water-insoluble polymers are disclosed. Such compositions may also contain additional quaternary ammonium compounds or other ionic surfactants not reacted with heparin and may also contain quaternary ammonium compound(s) or other ionic surfactants reacted with antibiotics or other ionic or nonionic pharmaceutical agents.

46 Claims, No Drawings

COATING COMPOSITIONS COMPRISING PHARMACEUTICAL AGENTS

This is a continuation of application Ser. No. 07/662,452, filed Feb. 28, 1991, now abandoned, which is a continuation-in-part of application Ser. No. 07/551,924, filed Jul. 12, 1990, now abandoned, which is a continuation-in-part of application Ser. No. 07/430,340, filed Nov. 2, 1989, now U.S. Pat. No. 5,069,899.

BACKGROUND OF THE INVENTION

Many kinds of polymer compositions have been used in the field of medical supplies. These compositions have not always exhibited anti-thrombogenic, anti-microbial, or other biocompatible characteristics when used in prosthetic and therapeutic apparatuses for handling or being in contact with blood or blood components or other bioresponse under conditions where clotting would tend to occur, such as artificial blood vessels, catheters, artificial hearts, fluid drainage, suction/aspiration and artificial kidneys.

When blood is brought in contact with metal, glass, plastic or other similar surfaces, it tends to clot in a short time unless certain precautions are taken. One common precaution currently in widespread use is the treatment of the surface with heparin or with heparin reacted with quaternary ammonium compounds. Such heparin compounds are known to have anti-coagulant effects when in contact with blood. The presence of the aforementioned heparin compounds on the surface imparts anti-thrombogenic characteristics. However, previously known heparinization or compositions have not been adequate because of the short time of anti-thrombogenic activity, at most a few days in vivo (I. S. Hersch, et al, J. Biomed., Mater. Res. Symposium I, 99–104 (1971); K. Amplatz, "A Simple Non-Thrombogenic Coating", Invest. Radiology, July, August, 1971, Vol. 6 or because the anti-thrombogenic characteristic was reduced to a very low level in order to make it resistant to removal by reacting it with quaternary ammonium polymers (U.S. Pat. No. 3,844,989).

It is therefore, an object of the present invention to provide novel anti-thrombogenic/polymer/heparin compound compositions or mixtures which prevent blood clotting for a relatively long period of time (over one month), and which have the same high degree of anti-thrombogenic characteristics as the non-polymerized heparin-quaternary ammonium compounds, and thus provide excellent properties for use as medical materials for coatings on artificial blood vessels, catheters, artificial hearts, artificial kidneys, etc.

Another object of the present invention is to provide novel anti-microbial surfaces which contain antibiotic agents which are entrained in the surface in such a way as to be gradually released in vivo to provide effective anti-microbial action over a longer time than was previously possible when using these agents. Typical agents useful in this embodiment of the invention include penicillins, cephalosporins, aminoglycosides, quinolones, sulfonoamides, tetracyclines, etc. While effective anti-microbial agent concentrations are achieved near the coated device surface, low systemic levels result, unlike where systemic antibiotic administration is required to combat infections caused by an implanted device.

SUMMARY OF THE INVENTION

The anti-thrombogenic, anti-microbial, pharmaceutical agent compositions (mixtures) of this invention comprise heparin-quaternary ammonium compounds and/or other ionic pharmaceutical agent-ionic surfactant compounds mixed with water-insoluble polymers. Pharmaceutical agents that are not reacted with ionic surfactants may also be used, providing that they have the appropriate solubility profile namely that they are soluble in organic solvents. They may also contain some hydrophilic polymers, but the mixture would still be water-insoluble after coating and drying. The water-insoluble polymers of this invention range from hydrophobic polymers to ones that are fairly hydrophilic, but are nevertheless essentially water-insoluble after being coated on a substrate and dried. A single polymer or mixture(s) of different polymers may be used to accomplish the invention. The heparin-quaternary ammonium compound may be mixed in a solution with the water-insoluble polymer, or it may be coated on top of a coating of the water-insoluble polymer(s), which is applied to the surface beforehand. In the latter case, a solvent must be added that is a mutual solvent for both the heparin-quaternary ammonium compound and the water-insoluble polymer(s) so that some mixing occurs between the two layers. In still another case, it is possible to coat the heparin-quaternary ammonium compound directly on the water-insoluble plastic surface, and incorporate a mutual solvent for both the plastic surface and the heparin-quaternary ammonium compound, so that some mixing occurs between the plastic surface and the heparin-quaternary ammonium compound.

Various combinations of these three systems would be obvious to one skilled in the art. The mixtures of the water-insoluble polymer(s) and heparin-quaternary ammonium compounds of this invention are substantially more resistant to removal or deactivation in human and animal body fluids such as blood or plasma than the heparin-quaternary ammonium compounds by themselves.

Typical examples of polymers suitable for use with the present invention are as follows: Water insoluble cellulose esters such as cellulose acetate, cellulose acetate butyrate, cellulose acetate propionate, and cellulose nitrate; polyurethane resins including polyether and polyester grades. Exemplary of the polyurethane is the reaction product of 2,4-tolylene diisocyanate and position isomers thereof, 4,4'-diphenylmethane diisocyanate and position isomers thereof, polymethylenepolyphenyl isocyanate, or 1,5-napthylene diisocyanate with 1,2-polypropylene glycol, polytetramethylene ether glycol, 1,4-butanediol, 1,4-butylene glycol, 1,3-butylene glycol, poly(1,4-oxybutylene)glycol, caprolactone, adipic acid esters, phthalic anhydride, ethylene glycol, 1,3-butylene glycol, 1,4-butylene glycol or diethylene glycol. Acrylic polymers such as ethyl and methyl acrylate and methacrylate; condensation polymers such as those produced by sulfonoamides such as toluenesulfonamide and aldehydes such as formaldehyde; and isocyanate compounds. Exemplary of the isocyanate compounds are polymethylenepolyphenyl isocyanate, 4,4'-diphenylmethane diisocyanate and position isomers thereof, 2,4-tolylene diisocyanate and position isomers thereof, 3,4-dichlorophenyl disocyanate and isoferrone isocyanate. Adducts or prepolymers of isocyanates and polyols such as the adduct of trimethylolpropane and diphenylmethane diisocyanate or tolylene diisocyanate are suitable. For further examples of polyisocyanates, see "Encyclopedia of Polymer Science and Technology", H. F. Mark, N. G. Gaylord and N. M. Bikales (eds.) (1969) incorporated herein by reference.

Typical quaternary ammonium compounds that can be reacted with heparin for use in this invention include benzalkonium chloride, tridodecylmethylammonium chloride, cetylpyridinium chloride, benzyldimethylstearylammonium chloride, benzylcetyldimethylammonium chloride, etc.

DETAILED DESCRIPTION OF THE INVENTION

The compositions of the present invention are first dissolved in solvent mixtures that are co-solvents for the mixtures of non-volatile components and which allow compatible homogenous films of the components to be cast. Such films when dried will typically appear as a clear film or films of very slight turbidity indicating that the non-volatile components have been deposited in a substantially homogenous manner. Typical solvents comprise alcohols, ketones, esters, aromatics, pyrrollidones, carboxylic acids, amides, and other organic solvents used alone or in appropriate mixtures as required, and which bring about the basic compatibility of the non-volatile components to be expressed. Typical surfaces which can be coated include plastic, metal and glass.

The heparin-quaternary ammonium compounds may be prepared in the conventional manner by any known prior art technique. For example, a heparin-benzalkonium chloride compound can be prepared by mixing approximately equal volumes of a 10% (by wt.) aqueous solution of sodium heparin with an approximately 17% (by wt.) solution of benzalkonium chloride (i.e., Zephiran from Winthrop-Breon Laboratories), and then washing the residual sodium chloride out with distilled or deionized water. Such preparations are disclosed in "A Simple Non-Thrombogenic Coating", K. Amplatz, Invest., Radiology, July, August, 1971, Vol. 6, which is incorporated herein by reference. It should be understood, however, that the invention is not limited to the heparin-quaternary ammonium compounds cited in the above reference.

In most cases, all the components are incorporated into a single solution so that the surface treatment can be accomplished with a single application. However, the treatment can also be applied in two steps. For example, the water-insoluble polymer(s) can be applied in one application and the heparin-quaternary ammonium compound can be applied to the water-insoluble polymer. Some mutual solvent(s) for the water-insoluble polymer and heparin-quaternary ammonium compound that makes two components compatible should be included in the overcoat application to accomplish the objective of the invention. For example, dimethylacetamide (DMA) effectively accomplishes this objective as shown in Example 1. A variant on this approach would involve application of the water-insoluble polymer(s) followed by application of a solution containing some water-insoluble polymers and some heparin-quaternary ammonium compound. Some heparin-quaternary ammonium compounds may also be added to the first application. Typical concentrations of heparin-quaternary ammonium compound in the coating solutions range from about 0.1% to 20% by weight. Preferred concentrations range from 0.5% up to 4%. Use of higher concentrations of heparin-quaternary ammonium compounds in the solutions does not enhance performance and is therefore not very useful or desired. Lower concentrations than those disclosed above reduce the anti-thrombogenicity of the layers.

Typical concentrations of the water-insoluble polymers in the coating solution range from about 0.01% to 20% by weight. Preferred concentrations range from about 0.2% to 3%. Higher concentrations tend to mask the anti-thrombogenic characteristics of the layers. Lower concentrations tend to allow the layer to be extracted more easily. The composition of the final costing may have the heparin quaternary compound present in a concentration of about 0.5 to 99.5 percent by weight with the balance of the composition comprising essentially the water-insoluble polymer.

ANTI-THROMBOGENICITY TEST

The following in vitro test was used to evaluate anti-thrombogenicity: 10 mm×75 mm glass test tubes were charged with 0.5 gm of reconstituted human plasma which had been kept refrigerated since collection. The test tubes were equilibrated in a 37° C. incubator for 10–30 minutes. Next, 0.1 g of 0.10 M $CaCl_2$ was added, and the test tube was manually swirled to achieve complete mixing. Immediately after swirling, 4½" long sections of 7 French tubing (either coated with one of the anti-thrombogenic systems of the present invention, or uncoated controls) were dropped into the plasma in each tube, taking care to ensure that the sample pieces were completely immersed in the plasma. The tubes were maintained in the 37° C. incubator and were checked for clotting at one minute intervals by removing them from the incubator and tilting them. Before clotting, the liquid flows in the test tube, but it gels and does not flow once it has clotted. Typical clotting times for plasma containing untreated polyurethane tubing range from six minutes to 15 minutes. Samples made according to this invention prevent clotting in this test. It was found that if the plasma did not clot after standing overnight, it would usually not clot for up to four weeks. Therefore, tests were usually discontinued if they had not clotted after standing overnight. Typical samples prepared by this invention did not clot when tested before plasma extraction, and retained their anti-clotting activity after 28 or more days of extraction in plasma. Devices coated with heparin-benzalkonium chloride or heparin-tridodecylmethylammonium chloride do not clot when tested before extraction in plasma, but lose their anti-thrombogenicity after plasma extraction of two hours or less. Heparinized quaternary polymers (HQP), such as those prepared according to U.S. Pat. No. 3,844,989 and used on catheters marked under the trademark ANTHRON by Toray Medical Co. Ltd., show only slight anti-thrombogenicity. For example, when tested against heparin-benzalkonium chloride (HBAC), the HBAC sample prevented clotting of the plasma overnight, while the control clotted in five minutes and the HQP sample clotted in seven minutes before plasma extraction, and showed no improvement in anti-thrombogenicity compared to the untreated polyurethane control after 12 hours of plasma extraction.

The following examples are intended to illustrate various preferred embodiments of the present invention.

EXAMPLE 1

Polyurethane 7 French tubing was coated with a solution containing the following ingredients and dried for 20 minutes at 65° C.

| | |
|---|---|
| Polyvinylpyrrolidone | .006 g |
| Isopropanol | 1.0 g |
| Nitrocellulose | 1.6 g |
| Ethylacetate | 1.2 g |
| Rosin ester | .5 g |
| Butylacetate | 4.8 g |
| Dimethylacetamide | 1.5 g |
| Ethyl-3-ethoxy propionate | 6.1 g |

The tubing was then overcoated with a solution containing the following ingredients and then dried for 20 minutes at 65° C.

| | |
|---|---|
| Isopropanol | 9.85 g |
| Dimethylacetamide | 1.00 g |

| | |
|---|---|
| Heparin-benzalkonium chloride | .15 g |

This sample was compared to a sample of polyurethane tubing which was coated with heparin-benzalkonium chloride (1.8% w/v in isopropanol) as follows. The samples were dipped in a Gentian Violet dye solution and then rinsed in hot running water. The sample coated with heparin-benzalkonium chloride (HBAC) in isopropanol lost most of the surface dye stain in less than 20 seconds, indicating that most of the HBAC had been washed off. The sample of the present invention that had the nitrocellulose undercoat and contained DMA in the HBAC overcoat, retained the dye stain much longer indicating that it is much more resistant to removal.

EXAMPLE 2

Polyurethane 7 French tubing was coated with a solution consisting of:

| | |
|---|---|
| Methylethylketone | 5.0 g |
| Heparin-benzalkonium chloride | 0.33 g |
| Isopropanol | 3.7 g |
| Ethyl-3-ethoxy propionate | .6 g |
| Butyl acetate | .5 g |
| ½ sec. nitrocellulose | .16 g |
| Ethyl acetate | .1 g |
| Rosin ester | .05 g |

The samples were dried at 75° C. for 30 minutes. Samples were then extracted in human plasma at 37° C. for 7, 10, 21, or 28 days and then tested for anti-clotting properties. The following results were obtained.

| Sample | Clotting time |
|---|---|
| Uncoated control | 12 minutes |
| Above sample, without extraction in plasma | Did Not Clot |
| Above sample, after 7 days extraction in plasma | Did Not Clot |
| Above sample, after 10 days extraction in plasma | Did Not Clot |
| Above sample, after 21 days extraction in plasma | 24 minutes |
| Above sample, after 28 days extraction in plasma | 20 minutes |

The above results show that the samples are still exhibiting effective anti-clotting activity on the device surface where it is most needed and that clots are unlikely to form on the treated surfaces, even after 28 days of extraction. This level of anti-clotting activity is stronger even after 28 days of plasma extraction than the anti-clotting levels achieved under these test conditions with surfaces treated according to the compositions taught by U.S. Pat. No. 3,844,989.

EXAMPLE 3

The following solution was coated on polyurethane 7 French tubing and dried at 75° C. for 20 minutes.

| | |
|---|---|
| Methylethylketone | 5 g |
| 8.3% heparin-benzalkonium chloride in isopropanol | 5 g |
| Cellulose Acetate Butyrate - 3A solution* | 1.5 g |
| *3A solution | |
| Ethyl-3-ethoxy propionate | 30.3 g |
| Butylacetate | 24.2 g |
| Ethyl acetate | 6.1 g |
| Rosin ester | 1.5 g |
| Isopropanol | 3.5 g |
| ½ sec. Cellulose acetate butyrate | 8.0 g |

Coated samples were tested for anti-clotting activity, and also for resistance to removal by dyeing with Gentian Violet dye and then rinsing with hot running water. The sample was compared to a coating of heparin-benzalkonium chloride without any cellulose ester polymer additive.

Results: The sample did not clot in the clotting test. In the hot water rinse test, the heparin-benzalkonium chloride coating without cellulose resin was completely removed in a few seconds. Hot water rinsing did not remove the above coating which contained cellulose acetate butyrate polymer.

EXAMPLE 4

Polyurethane 7 French tubing was coated as in Example 3 except that cellulose acetate butyrate was replaced with cellulose acetate propionate. The sample was tested for anti-clotting activity and resistance to removal in hot water. Results were comparable to those with Example 3.

EXAMPLE 5

Polyurethane 7 French tubing was coated with the following solution and dried at 80° C. for 20 minutes.

| | |
|---|---|
| Methylethylketone | 5 g |
| 8.3% heparin-benzalkonium chloride in isopropanol | 4 g |
| Cellulose acetate propionate 5A solution* | 2 g |
| *5A solution | |
| Ethyl-3-ethoxy propionate | 30.3 g |
| Butylacetate | 24.2 g |
| Ethylacetate | 6.1 g |
| Rosin ester | 2.5 g |
| Isopropanol | 3.5 g |
| ½ sec. cellulose acetate propionate | 8.0 g |

The coated sample was extracted in plasma at 37° C. for four hours and tested for anti-microbial activity by pressing it into gelled Difco Plate Agar which was spiked with Staphylococcus epidermidis (ATCC 12228) and then incubated overnight at 32°–35° C. A sample of polyurethane tubing that was coated with heparin-benzalkonium chloride without cellulose polymer was extracted in plasma at 37° C. for four hours for comparison. The sample which contained cellulose acetate propionate (CAP) polymer showed a significant zone of inhibition while the sample made without CAP resin showed no zone of inhibition, demonstrating that the incorporation of cellulose ester polymer effectively increases resistance to removal of the coating when extracted in human plasma.

EXAMPLE 6

Example 5 was repeated, except that the solution contained 1.5 gm of 10.7% (wt. %) nitrocellulose solution in place of the 2.0 grams of 10.7% (wt. %) CAP solution. Samples of polyurethane tubing coated with this solution were extracted in plasma at 37° C. for four hours or 18 hours. They were then tested for anti-microbial activity using the same zone of inhibition test as used in Example 5. The tests showed zones of inhibition after both extraction intervals. The sample extracted for four hours has a larger zone of inhibition than the sample that was extracted for 18 hours.

EXAMPLE 7

The following solution was coated on polyurethane 7 French tubing and dried at 80° C. for 20 minutes. A control was made by coating a sample of the tubing with a 5% w/v solution of Tridodecylmethylammonium chloride (TDMAC).

| | |
|---|---|
| Methylethylketone | 5 g |
| 8.3% heparin-benzalkonium chloride in isopropanol | 4 g |
| 7A solution* | 1.5 g |
| *7A solution | |
| Ethyl-3-ethoxy propionate | 30.3 g |
| Butylacetate | 24.2 g |
| Ethyl acetate | 6.1 g |
| Rosin ester | 2.5 g |
| Isopropanol | 3.5 g |
| ½ sec. Nitrocellulose | 8.0 g |

Both samples were then immersed for 30 minutes in a 5% aqueous solution of penicillin G and then air dried overnight. The coated samples were then extracted for 18 hours in human plasma at 37° C. They were removed from the plasma, rinsed in running deionized water and then tested for anti-microbial activity as in Example 5. The sample containing nitrocellulose showed a strong zone of inhibition while the sample without nitrocellulose showed no zone of inhibition.

EXAMPLE 8

Example 7 was repeated, except that TDMAC was added to the coating solutions as follows:

| | |
|---|---|
| Example 8 | .025 gm TDMAC added |
| Example 8A | .075 gm TDMAC added |

Both samples showed a strong zone of inhibition after the 18 hours plasma extraction and appeared to be substantially comparable to Example 7.

EXAMPLE 9

Polyurethane 7 French tubing was coated with the following solution.

| | |
|---|---|
| Heparin tridodecylmethylammonium chloride | 0.2 g |
| Isopropanol | 2.6 g |
| Methylethylketone | 2.5 g |
| 7A Solution | 0.7 g |

This coated sample was tested for clotting and did not clot. It was very resistant to removal in hot running water.

EXAMPLE 10

Polyurethane 7 French tubing was coated with a solution containing the following ingredients and dried at ambient temperature for 60 minutes:

| | |
|---|---|
| Methylethlyketone | 5.3 g |
| Heparin-benzalkonium chloride | 0.31 g |
| Isopropanol | 3.4 g |
| Acrylic resin | 0.2 g |
| Rosin ester | 0.2 g |
| Tridodecylmethylammonium chloride | 0.4 g |
| Xylene | 0.14 g |

| | |
|---|---|
| Butanol | 0.05 g |

Samples were then extracted in plasma at 37° C. for 4, 24 and 120 hours and compared to uncoated polyurethane tubing for anti-clotting activity. The results were as follows:

| Sample | Clotting Time |
|---|---|
| Uncoated control | 9 minutes |
| Above sample, without extraction in plasma | Did Not Clot |
| Above sample, after 4 hours extraction in plasma | Did Not Clot |
| Above sample, after 24 hours extraction in plasma | Did Not Clot |
| Above sample, after 120 hours extraction in plasma | Did Not Clot |

The above coated sample was resistant to removal by hot running water.

EXAMPLE 11

Polyurethane 7 French tubing was coated with a solution containing the following ingredients and dried 15 minutes at 75° C.:

| | |
|---|---|
| Methylethylketone | 5.6 g |
| Heparin-benzalkonium chloride | 0.33 g |
| Isopropanol | 3.5 g |
| Polyurethane resin | 0.24 g |
| Polyisocyanate resin | 0.19 g |
| Ethyl acetate | 0.19 g |

Samples were extracted in plasma at 37° C. for 72 hours and then tested for anti-clotting properties. A sample of polyurethane tubing which was coated with heparin-benzalkonium chloride (1.8% w/v in isopropanol) was also extracted in plasma at 37° C. for 72 hours for comparison. The following results were obtained:

| Sample | Clotting Time |
|---|---|
| Uncoated control | 13 minutes |
| Above sample, after 72 hours extraction in plasma | Did Not Clot |
| Sample coated with heparin-benzalkonium chloride in isopropanol, after 72 hours extraction in plasma | 7 minutes |

The above coating was also resistant to removal by hot running water.

EXAMPLE 12

Polyurethane 7 French tubing was coated with a solution containing the following ingredients and dried for 20 minutes at 70° C.

| | |
|---|---|
| Methylethylketone | 5.9 g |
| Heparin-benzalkonium chloride | 0.32 g |
| Isopropanol | 3.5 g |
| Polyurethane resin | 0.14 g |
| Polyisocyanate resin | 0.07 g |
| Ethylacetate | 0.07 g |

Samples were then extracted in human plasma at 37° C. for 3, 24, and 48 hours and then tested for anti-clotting properties. The following results were obtained:

| Sample | Clotting Time |
|---|---|
| Uncoated control | 8 minutes |
| Above sample, after 3 hours extraction in plasma | Did Not Clot |
| Above sample, after 24 hours extraction in plasma | Did Not Clot |
| Above sample, after 48 hours extraction in plasma | 9 minutes |

EXAMPLE 13

Polyurethane 7 French tubing was coated with a solution containing the following ingredients and dried for 20 minutes at 70° C.

| | |
|---|---|
| Methylethylketone | 6.1 g |
| Heparin-benzalkonium chloride | 0.32 g |
| Isopropanol | 3.5 g |
| Polyurethane resin | 0.07 g |
| Polyisocyanate resin | 0.04 g |
| Ethylacetate | 0.04 g |

Coated tubing was then extracted in plasma for 3 and 24 hours and then tested for anti-clotting behavior. The following results were obtained:

| Sample | Clotting Time |
|---|---|
| Uncoated control | 8 minutes |
| Above sample, after 3 hours extraction in plasma | Did Not Clot |
| Above sample, after 24 hours extraction in plasma | 9 minutes |

EXAMPLE 14

Polyurethane 7 French tubing was coated with a solution containing the following ingredients and dried for 20 hours at 55° C.

| | |
|---|---|
| Heparin tridodecylmethylammonium chloride | 0.32 g |
| Dimethylacetamide | 6.2 g |
| Toluene | 2.0 g |
| Petroleum ether | 1.5 g |

The coated tubing was extracted in human plasma at 37° C. for 1, 2, 3 and 6 days and then tested for anti-clotting properties.

| Sample | Clotting Time |
|---|---|
| Uncoated sample | 10 minutes |
| Above sample, after 1 day extraction in plasma | Did Not Clot |
| Above sample, after 2 days extraction in plasma | Did Not Clot |
| Above sample, after 3 days extraction in plasma | Did Not Clot |
| Above sample, after 6 days extraction in plasma | Did not Clot |

The preceding examples, together with controls, show clearly that heparin-quaternary ammonium compounds and other pharmaceutical agents that are not polymeric can be made more resistant to removal or deactivation in various body fluids such as whole blood or plasma (including human) by mixing with appropriate water-insoluble polymers. Coatings made from normal heparin-quaternary ammonium compounds by themselves using solvents that do not cause mixing with the substrate, such as heparin-benzalkonium chloride, or heparin tridodecylmethylammonium chloride show little anti-thrombogenicity after soaking in human plasma for only a few hours. The heparin-TDMAC compound continues to show anti-thrombogenicity somewhat longer than the benzalkonium chloride compound, but both exhibit almost no anti-thrombogenicity after soaking in human plasma for a few hours. The incorporation of water-insoluble polymers according to the present invention, and as shown in the examples, greatly extends the time for which coating samples can be soaked in human plasma and still show substantially levels of anti-thrombogenicity. For instance, some samples were found to show anti-thrombogenicity even after soaking in human plasma for 28 days.

On the other hand, when quaternary ammonium polymers are reacted with heparin, the coating remains on the surface even after long periods of soaking in body fluids such as human plasma, but the anti-thrombogenicity is not as strong either before soaking or after soaking for up to 28 days in human plasma, as in the samples made according to this invention. It is further noted that by water-insoluble polymers we are implying that they are water-insoluble after a film is cast and dried, and include water-insoluble polymers that may be hydrophilic, but nevertheless cause the heparin-quaternary ammonium compounds to remain anti-thrombogenic after prolonged soaking in body fluids.

In a further embodiment of the present invention, it has been found that it is possible to react an antibiotic or other pharmaceutical agent such as penicillin, ticarcillin, cefotoxin, cephalosporins, oxacillin, and carbonicillin that contains a positive inorganic ion such as sodium with a quaternary ammonium compound such as benzalkonium chloride or (TDMAC) to produce an ionic antibiotic that is soluble in organic solvents and is miscible with hydrophobic water insoluble polymers. In this embodiment, the resulting polymer mixture would not contain an anti-thrombogenic agent such as heparin. It is also possible to react other antibiotics or pharmaceutical agents that contain a negative ion such as chloride with surfactants that contain a negative organic ion such as sodium laurylsulfate to again convert a water soluble antimicrobial agent or other pharmaceutical agent into one that is soluble in organic solvents and miscible with hydrophobic water insoluble polymers. It is also possible to incorporate pharmaceutical agents without reaction with ionic surfactants if the pharmaceutical agent has low water solubility and is soluble in organic solvents and miscible with the hydrophobic water insoluble polymers of the present invention. When these organic solvent soluble agents are nixed with polymers of this invention, they can be rendered much more resistant to removal in plasma from the surface of an article coated with them than if they are coated on the surface without the polymer.

By using antibiotics or other pharmaceutical agents that are, soluble in organic solvents, or by making the antibiotic or other pharmaceutical agent soluble in organic solvents and miscible with the water insoluble polymers of this invention, it makes it possible to incorporate useful pharmaceuticals such as antibiotics onto medical devices at the time of manufacture. The pharmaceuticals are available at the surface of the device in efficacious concentrations, over a useful period such as several days to weeks. At the same time, while the pharmaceuticals are present in useful concentrations where they are wanted on the device surface, they are not present in high concentration systematically so that typical side effects normally associated with various pharmaceuticals are unlikely.

The polymer can be mixed with the pharmaceutical agent and then coated, or the polymer or agent can be coated first and then overcoated with the other agent. The single coating of a mixture of polymer and pharmaceutical agent would normally be preferred because it would involve only a single coating and because the ratio of pharmaceutical agent to polymer can be controlled more precisely. Such mixtures of pharmaceutical agents and polymers would not be anti-thrombogenic unless they also contained an anti-thrombogenic agent such as heparin. However, the coatings do show strongly the desired effect of the incorporated pharmaceutical agent such as anti-microbial activity. The presence of certain polymers also has the added benefit of enhancing the stability of the pharmaceutical agent to a sterilization process such as exposure to ethylene oxide.

The antibiotic-surfactant compound or other pharmaceutical agent is present in a concentration of about 0.5% to 99.5% by weight with the balance comprising the water-insoluble polymer. The concentration of the water-insoluble polymer is typically about 0.01% to 40% by weight and the concentration of antimicrobial-surfactant compound is about 0.01% to 40% by weight of the coating solution.

The following example demonstrates how the system works.

In Examples 15–18, $^{14}$C-penicillin G sodium salt was reacted with tridodecylmethylammonium chloride (TDMAC) using procedures similar to those previously described in the Background Of The Invention, see A. Amplatz, "A Simple Non-Thrombogenic Coating", Invest. Radiology, July, August, 1971, Vol. 6, which is incorporated herein by reference.

A typical method of preparation for the pharmaceutical agent-TDMAC compounds of the present invention is as follows:

Seventeen grams TDMAC is dissolved in 60 ml isopropanol, and diluted with 40 ml distilled water. Next, dissolve 10 grams of the sodium salt of the pharmaceutical agent (SPA) in 100 ml distilled water. Mix equal volumes of both liquids and shake vigorously for ten or so seconds to ensure complete mixing and reaction.

Next, vacuum filter over filter paper, collect the compound off the paper, and place in a centrifuge jar with 1 volume of water, shake for 30 minutes, and vacuum filter again on filter paper. The wash is repeated twice more. The SPA-TDMAC is dried in an oven at 60° C.

Using this basic procedure, it is obvious to one skilled in the art that organic salts can be made from many or most ionic pharmaceutical agents by mixing them together with an appropriate ionic surfactant, and washing out the water-soluble salt residue with water. These compounds are soluble in organic solvents and typically have very low solubility constants so that when mixed with the polymers of this invention, constant and efficacious concentrations of the pharmaceutical agent (5) will be available on the coated surface in vivo over an extended period.

The resultant $^{14}$C-penicillin-TDMAC prepared by the above method is soluble in various organic solvents and has extremely low water solubility but is still ionic. The $^{14}$C-penicillin-TDMAC was then mixed with selected polymers and coated on both silicone and polyurethane tubing. The coatings were then extracted in plasma for one day or 5 days and compared to non-extracted samples by scintillation counting to determine how much penicillin remained on the surface in the coating after extraction. Some samples were exposed to an ethylene oxide sterilization cycle and tested by zone of inhibition, to show whether the polymer improved the resistance of the antibiotic to degradation when exposed to ethylene oxide.

EXAMPLE 15

The $^{14}$C-penicillin-TDMAC was mixed with cellulose nitrate dissolved in a solvent mixture containing ethanol, isopropanol, ethylacetate and toluene. The solution has the following composition:

| | |
|---|---|
| Nitrocellulose | 1.8 g |
| Isopropanol | .8 g |
| Toluene | 24.3 g |
| Ethyl acetate | 5.1 g |
| Camphor | .5 g |
| Dibutylphthalate | .7 g |
| $^{14}$C-penicillin-TDMAC | 2.0 g |

The solution was coated on both silicone and polyurethane tubing and dried. Some coated samples were then extracted in plasma for 24 hours or five days. After plasma extraction, the samples were measured by scintillation counting and were compared to unextracted samples to show how much $^{14}$C-penicillin-TDMAC remained. The following results were obtained.

| | Not Extracted | After 24 hrs. Extraction | After Five Days Extraction |
|---|---|---|---|
| Silicone tubing | 48 μg/cm$^2$ | 30 μg/cm$^2$ | 6 μg/cm$^2$ |
| Polyurethane tubing | 36 μg/cm$^2$ | 43 μg/cm$^2$ | 38 μg/cm$^2$ |

When the $^{14}$C-penicillin-TDMAC was coated without polymer, it was removed from the tubing surface in a few hours. These results clearly show how incorporation of this polymer into the coating dramatically extends the elution time from the surface when extract in plasma.

EXAMPLE 16

Example 15 was repeated using Silastic silicone resin in 1,1,1,-Trichloroethane in place of the nitrocellulose solution. The solution has the following composition:

| | |
|---|---|
| Silastic Polymer | 1.3 g |
| 1,1,1-Trichloroethane | 28.7 g |
| Toluene | 8.0 g |
| $^{14}$C-penicillin-TDMAC | 2.0 g |

This sample was tested for resistance to extraction in plasma, and for resistance to degradation by ethylene oxide sterilization.

| | Not Extracted | After 24 hrs. Extraction | After Five Days Extraction |
|---|---|---|---|
| Silicone tubing | 68 μg/cm$^2$ | 33 μg/cm$^2$ | 27 μg/cm$^2$ |
| Polyurethane tubing | 18 μg/cm$^2$ | 8 μg/cm$^2$ | 6 μg/cm$^2$ |

These results show that incorporation of Silasticβ resin into the coating extends the elution time of the antibiotic in plasma to several days compared to a few hours without the resins.

After exposure to a typical ethylene oxide sterilization (ETO) cycle, the samples were tested by classic zone of inhibition testing. This was done by placing a sample (sterilized or non-sterilized) onto a layer of agar containing bacteria and then incubated. The results are reported as the size in mm of the clear zone surrounding the coated article which results from the antimicrobial activity of active $^{14}$C-penicillin-TDMAC.

|  | Before ETO Exposure | After ETO Exposure |
|---|---|---|
| With Silasticβ | 11 | 10 |
| Without polymer | 26 | 0 |

This result clearly demonstrates how incorporation of Silasticβ polymer into the $^{14}$C-penicillin-TDMAC coating greatly increases the resistance of the antibiotic to degradation caused by exposure to ethylene oxide.

EXAMPLE 17

Example 15 was repeated using polyvinylbutyral (PVB) polymer in toluene in place of the nitrocellulose solution. The solution has the following composition:

| Polyvinylbutryral | 1.5 g |
|---|---|
| Toluene | 31.5 g |
| $^{14}$C-penicillin-TDMAC | 2.0 g |

This was coated on silicone and polyurethane tubings, dried, and then tested for resistance to extraction in plasma, and resistance to degradation during an ethylene oxide sterilization by zone of inhibition. The following results were obtained.

|  | Not Extracted | After 24 hrs. Extraction | After Five Days Extraction |
|---|---|---|---|
| Silicone tubing | 18 μg/cm$^2$ | 18 μg/cm$^2$ | 16 μg/cm$^2$ |
| Polyurethane tubing | 12 μg/cm$^2$ | 13 μg/cm$^2$ | 10 μg/cm$^2$ |

|  | Before ETO Sterilization | After ETO Sterilization |
|---|---|---|
| With PVB Polymer | 25 mm | 15 mm |
| Without Polymer | 26 mm | 0 |

Clearly, PVB polymer provides significant stabilization to $^{14}$C-penicillin-TDMAC against degradation caused by exposure to ethylene oxide.

EXAMPLE 18

Example 1 was repeated using cellulose acetate butyrate polymer (CAB) in place of the nitrocellulose solution. The solution has the following composition:

| Cellulose Acetate Butyrate | 2.0 g |
|---|---|
| Ethyl acetate | 8.0 g |
| Toluene | 17.0 g |
| $^{14}$C-penicillin-TDMAC | 2.0 g |

This solution was coated on silicone and polyurethane tubings, dried, and tested for resistance to extraction from the surface in plasma. It was also tested for resistance to degradation from ethylene oxide exposure. The following results were obtained.

|  | Not Extracted | After 24 hrs. Extraction | After Five Days Extraction |
|---|---|---|---|
| Silicone tubing | 33 μg/cm$^2$ | 12 μg/cm$^2$ | 17 μg/cm$^2$ |
| Polyurethane tubing | 20 μg/cm$^2$ | 12 μg/cm$^2$ | 7 μg/cm$^2$ |

CAB polymer clearly increases the resistance of $^{14}$C-penicillin-TDMAC to extraction in plasma.

|  | Before ETO Sterilization | After ETO Sterilization |
|---|---|---|
| With CAB Polymer | 31 mm | 31 mm |
| Without Polymer | 26 mm | 0 |

This result shows how CAB polymer provides substantial stabilization to $^{14}$C-penicillin-TDMAC against ETO induced degradation.

The foregoing Examples show how incorporation of these and/or other water insoluble polymers clearly improves resistance of pharmaceutical agents or pharmaceutical salts of organic ions to extraction in plasma and against the degradation effects from exposure to sterilization with ethylene oxide. At the same time, however, the incorporation of polymers still leaves effective concentrations of antibiotic or other pharmaceutical agent available at the coated surface as demonstrated by the zone of inhibition test results in Examples 16, 17 and 18.

It is expected that different polymers could be used together in a single solution/coating or in contiguous layers to further enhance performance and achieve specific results. We have also tested other polymers mixed with the pharmaceutical agents or organic ion salts of pharmaceuticals and found similarly useful improvement in resistance to extraction by plasma. These include polyisocyanates, acrylicpolymers, vinylacetate, and others.

Examples 19, 20, 21 and 22 demonstrate further how various drugs can be incorporated into coatings of the invention and are suitable for use on medical devices.

EXAMPLE 19

The following solution was made and coated on ¼" 1D, ¹⁄₁₆" wall thickness polyurethane rings and dried at 80° C.

| Cellulose acetate butyrate | 0.35 g |
|---|---|
| Norfloxacin | 0.17 g |
| Benzylalcohol | 1.58 g |
| Toluene | 1.57 g |
| Dimethylacetamide | 5.25 g |
| Butyl Acetate | 1.58 g |

Coated rings were then extracted in artificial urine at 37° C. and then tested for zone of inhibition vs. *E. coli*. The coating was still effective up to 35 days in the artificial urine. Coated samples sterilized by EtO were also effective against *E. coli*.

EXAMPLE 20

2 ml. sodium methotrexate (25 mg/ml) was placed in a test tube and 4 ml. Ethanol was added. The methotrexate precipitated out of solution. Tridodecylmethylammonium chloride was added and the test tube was swirled to mix the agents. The methotrexate quickly went into solution as the tridodecylmethylammonium salt. This mixture was shaken with an equal volume of toluene to separate the water and sodium chloride from the methotrexate tridodecylmethylammonium salt. The toluene layer separated on top and had the characteristic yellow color of methotrexate salts. The aqueous layer was clear and had no color. The toluene layer was diluted with an equal volume of 2% cellulose acetate butyrate in Butyrolactone. This was coated on a polyurethane catheter surface and produced a clear layer.

EXAMPLE 21

Three drops of 7.4% solution of gentamicin chloride in 62.5% water, 37.5% dimethylacetamide was diluted with 15 drops of glacial acetic acid, and 1.5 ml ethanol. Next, three drops of nitrocellulose in butyrolactone was added. This solution was clear, and produced a clear layer when coated and dried on glass.

EXAMPLE 22

The following solution was coated on glass and dried for 2 minutes at 80° C.

| | |
|---|---|
| Merbarone | 0.1 gm |
| Dimethysulfoxide | 1.98 gm |
| Cellulose acetate butyrate | 0.12 gm |
| Ethanol | 2.0 gm |

This solution was clear, and the dried layer on glass was also clear.

Other modifications and ramifications of the present invention would appear to those skilled in the art upon a reading of this disclosure. These are intended to be included within the scope of this invention.

What is claimed is:

1. A device comprising: a substrate, and a coating composition comprising a pharmaceutical agent in a concentration of from about 0.5% to about 99.5% by weight and a water-insoluble cellulose ester polymer, the coating composition being resistant to removal and having pharmaceutical activity under physiological conditions.

2. The device of claim 1 in which the water-insoluble cellulose ester polymer and the pharmaceutical agent are present in separate inner and outer layers and a therapeutically effective amount of the pharmaceutical agent is dispersed into the outer layer.

3. The device of claim 1 wherein the water insoluble cellulose ester polymer is selected from the group consisting of cellulose acetate propionate, cellulose acetate, cellulose acetate butyrate, cellulose nitrate, cellulose acetate phthalate, and mixtures thereof.

4. The device of claim 1 wherein the coating composition further comprises a plasticizing agent.

5. The device of claim 1 wherein the pharmaceutical agent is selected from the group consisting of an antithrombogenic material, an antibiotic material, an anticancer material, and mixtures thereof.

6. The device of claim 1 wherein the pharmaceutical agent comprises an antithrombogenic agent complexed with a quaternary ammonium compound.

7. The device of claim 1 wherein the pharmaceutical agent comprises a negatively charged antibiotic agent complexed with a quaternary ammonium compound.

8. The device of claim 1 wherein the pharmaceutical agent comprises a positively charged antibiotic agent complexed with an anionic surfactant.

9. The device of claim 1 wherein the pharmaceutical agent comprises an ionic antibiotic agent complexed with an ionic polymer.

10. The device of claim 1 wherein the pharmaceutical agent is ionic and the coating composition further comprises a surfactant which is capable of complexing the pharmaceutical agent.

11. The device of claim 10 wherein the surfactant comprises at least one compound selected from the group consisting of cationic quaternary ammonium compounds, pharmaceutically acceptable salts thereof, anionic organic acids, pharmaceutically acceptable salts thereof, and ionic polymers, and mixtures thereof.

12. The device of claim 10 wherein the surfactant is anionic.

13. The device of claim 12, in which the substrate is selected from the group consisting of glass, metal, polyurethane, silicone, and plastic.

14. The device of claim 1, in which the device is selected from the group consisting of a catheter, a needle, a fluid drainage device, a suction device, aspiration device, an artificial blood vessel, an artificial heart, and an artificial kidney.

15. The device of claim 1 wherein the pharmaceutical agent is non-ionic.

16. The device of claim 1 wherein the coating composition is free of any ionic surfactant.

17. The device of claim 1 wherein the pharmaceutical agent is ionic, and further comprising a surfactant.

18. The device of claim 1 wherein the pharmaceutical agent is anionic, and the surfactant is cationic.

19. The device of claim 1 wherein the pharmaceutical agent is cationic, and the surfactant is anionic.

20. The device of claim 1, the coating composition further comprising a substance selected from the group consisting of polyurethane, camphor, dibutylphthalate, and mixtures thereof.

21. The device of claim 1 wherein the pharmaceutical agent is a negatively charged substance complexed with a quaternary ammonium compound.

22. The device of claim 1 wherein the pharmaceutical agent is selected from the group consisting of penicillins, cephalosporins, carbapenems, and mixtures thereof.

23. The device of claim 1 wherein the pharmaceutical agent is selected from the group consisting of prostaglandin E-1, prostacyclin, iloprost, and mixtures thereof.

24. The device of claim 1 wherein the pharmaceutical agent is norfloxacin.

25. The device of claim 1 wherein the pharmaceutical agent is selected from the group consisting of methotrexate and merbarone.

26. The device of claim 10 wherein the surfactant is selected from the group consisting of cationic quaternary ammonium compounds pharmaceutically acceptable salts thereof, anionic organic acids, pharmaceutically acceptable salts thereof, ionic polymers, and mixtures thereof.

27. The device of claim 10 wherein the surfactant is selected from the group consisting of sodiumlaurylsulfate, dicetylphosphate, stearic acid, sodium stearate and mixtures thereof.

28. The device of claim 10 wherein the surfactant is selected from the group consisting of ionic polymers, polyacrylic acid, copolymers of methylvinylether/maleicanhydride, and mixtures thereof.

29. The device of claim 10 wherein the surfactant is selected from the group consisting of trioctadecylmethylammoniumchloride, tridodecylmethylammoniumchloride, benzalkoniumchloride, cetylpyridinium chloride, benzyldimethyletearylammonium chloride, and benzylcetyldimethylammonium chloride, and mixtures thereof.

30. The device of claim 29 wherein the surfactant is reacted with at least one material selected from the group consisting of heparin, an antibiotic, an anticancer compound, and mixtures thereof.

31. The device of claim 1, in which the coating further comprises polyvinylpyrrolidone.

32. A coated device produced by a process comprising:

(a) combining a pharmaceutical agent in a concentration of from about 0.01% to about 40%, a water-insoluble cellulose ester polymer in a concentration of from about 0.01% to about 40%, and an organic solvent to form a coating liquid, (b) placing a device in contact with the coating liquid, (c) removing the device from the coating liquid, and (d) removing the organic solvent to form a coating on the device, wherein the coating adheres to the device and has pharmaceutical activity under physiological conditions.

33. The coated device of claim 32 wherein the pharmaceutical agent is soluble in the solution of cellulose ester polymer and organic solvent without the presence of a surfactant.

34. The coated device of claim 32, in which the concentration of the pharmaceutical agent in the coating liquid is from about 0.1% to about 20%, and the concentration of the water-insoluble cellulose ester polymer in the coating liquid is from about 0.1% to about 20%.

35. The coated device of claim 32, in which the concentration of the pharmaceutical agent in the coating liquid is from about 0.5% to about 4%, and the concentration of the water-insoluble cellulose ester polymer in the coating liquid is from about 0.2% to about 3%.

36. A coated article produced by a process comprising:

preparing a polymer coating liquid comprising a water-insoluble cellulose ester polymer in a concentration of from about 0.01% to about 40%, and an organic solvent for the polymer, preparing a pharmaceutical coating liquid comprising a pharmaceutical agent in a concentration of from about 0.01% to about 40%, and an organic liquid, contacting an article with the polymer coating liquid, removing the article, and removing the organic solvent, and contacting the article with the pharmaceutical coating liquid, removing the article, and removing the organic liquid, to produce a coated article having an adherent, essentially water-insoluble coating with pharmaceutical activity under physiological conditions.

37. A coated article comprising:

a substrate; and a coating comprising a pharmaceutical agent in a concentration of from about 0.5% to about 99.5% by weight, and a water-insoluble cellulose ester polymer, the pharmaceutical agent being entrained in the cellulose ester polymer in such a way as to be gradually released under physiological conditions, to provide effective concentrations of the pharmaceutical agent at the surface of the coating over a useful period, and the coating being adherent to the substrate and essentially water-insoluble.

38. The coated article of claim 37 in which the coating is resistant to degradation from exposure to sterilization.

39. The coated article of claim 37, in which the coating further comprises polyvinylpyrrolidone.

40. The coated article of claim 37, the coating having inner and outer layers, the inner layer adhering to the substrate and comprising a cellulose ester, and the outer layer having an exposed outer surface and comprising a cellulose ester and a pharmaceutical agent.

41. The coated article of claim 40, the inner layer comprising cellulose ester and polyurethane, and the outer layer comprising cellulose ester, polyvinylpyrrolidone, and a pharmaceutical agent.

42. The coated article of claim 41, the inner layer further comprising a pharmaceutical agent.

43. The coated article of claim 40, the inner layer further comprising dibutylphthalate, camphor, or a mixture thereof.

44. The coated device of claim 32 in which the coating liquid comprises a pharmaceutical agent, a cellulose ester, polyurethane, dibutylphthalate, camphor, and a solvent selected from the group consisting of methyl ethyl ketone, ethyl acetate, butyl acetate, isopropanol, cyclohexanone, butyrolactone, and mixtures thereof.

45. The coated device of claim 44, the coating liquid further comprising polyvinylpyrrolidone.

46. The coated device of claim 44 in which the pharmaceutical agent is tridodecylmethylammonium heparinate.

\* \* \* \* \*